US006996430B1

(12) United States Patent
Gilboa et al.

(10) Patent No.: US 6,996,430 B1
(45) Date of Patent: Feb. 7, 2006

(54) METHOD AND SYSTEM FOR DISPLAYING CROSS-SECTIONAL IMAGES OF A BODY

(75) Inventors: Pinhas Gilboa, Haifa (IL); David Tolkowsky, Tel Aviv (IL)

(73) Assignee: Super Dimension LTD, Herzeliya (IL)

( * ) Notice: Subject to any disclaimer, the term of this patent is extended or adjusted under 35 U.S.C. 154(b) by 0 days.

(21) Appl. No.: 09/959,837

(22) PCT Filed: Dec. 12, 1999

(86) PCT No.: PCT/US99/26826

§ 371 (c)(1),
(2), (4) Date: Nov. 8, 2001

(87) PCT Pub. No.: WO01/12057

PCT Pub. Date: Feb. 22, 2001

Related U.S. Application Data

(60) Provisional application No. 60/148,693, filed on Aug. 16, 1999.

(51) Int. Cl.
*A61B 5/05* (2006.01)

(52) U.S. Cl. ............... 600/407; 600/411; 600/424; 600/427; 600/466

(58) Field of Classification Search ............... 600/407, 600/410, 424, 425, 427, 437, 462, 466, 436, 600/411, 467, 117; 128/899, 916; 324/207.15
See application file for complete search history.

(56) References Cited

U.S. PATENT DOCUMENTS

| | | | |
|---|---|---|---|
| 4,791,934 A | 12/1988 | Brunnett | |
| 5,383,454 A | 1/1995 | Bucholz | |
| 5,425,367 A * | 6/1995 | Shapiro et al. | ............. 600/424 |
| 5,558,091 A | 9/1996 | Acker et al. | |
| 5,668,844 A | 9/1997 | Webber | |
| 5,704,361 A | 1/1998 | Seward et al. | |
| 5,772,594 A | 6/1998 | Barrick | |
| 5,810,007 A | 9/1998 | Holupka et al. | |
| 5,871,445 A | 2/1999 | Bucholz | |
| 5,873,822 A | 2/1999 | Ferre et al. | |
| 5,891,034 A | 4/1999 | Bucholz | |
| 5,902,239 A | 5/1999 | Buurman | |
| 6,149,592 A * | 11/2000 | Yanof et al. | ............. 600/427 |
| 6,226,543 B1 * | 5/2001 | Gilboa et al. | ............. 600/407 |
| 6,289,235 B1 * | 9/2001 | Webber et al. | ............. 600/426 |

(Continued)

FOREIGN PATENT DOCUMENTS

WO    WO96/05768    2/1996

(Continued)

OTHER PUBLICATIONS

U.S. Appl. No. 09/463,176, filed Jan. 2000, Gilboa et al.

(Continued)

*Primary Examiner*—Shawna J. Shaw
(74) *Attorney, Agent, or Firm*—Mark M. Friedman

(57) ABSTRACT

This invention is a method of displaying cross-sectional images of a body so as to render the cross-sectional images more interpretable. The method is effected by using a first imaging device (110, 120), obtaining at least one cross-sectional image of a portion of the body, at least one cross-sectional image being defined by at least one first plane; and projecting each of at least one cross-sectional image of the portion of the body onto a predefined second plane, so as to obtain at least one projected cross-sectional image of the portion of the body, each of the at least one projected cross-sectional image becoming more interpretable by a user.

16 Claims, 3 Drawing Sheets

U.S. PATENT DOCUMENTS

| | | | |
|---|---|---|---|
| 6,558,333 B2 * | 5/2003 | Gilboa et al. | 600/466 |
| 2002/0193686 A1 * | 12/2002 | Gilboa | 600/424 |
| 2003/0074011 A1 * | 4/2003 | Gilboa et al. | 606/130 |
| 2003/0216639 A1 * | 11/2003 | Gilboa et al. | 600/424 |
| 2004/0006268 A1 * | 1/2004 | Gilboa et al. | 600/424 |

FOREIGN PATENT DOCUMENTS

WO     WO96/25882     8/1996

OTHER PUBLICATIONS

U.S. Appl. No. 09/463,177, filed Jan. 2000, Gilboa et al.

* cited by examiner

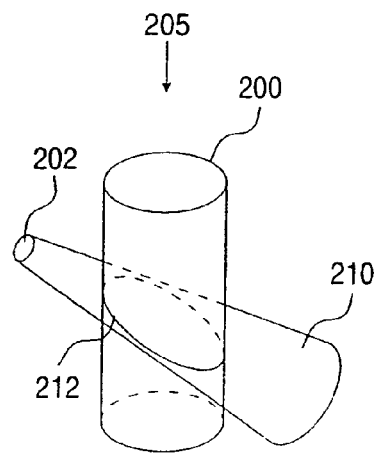
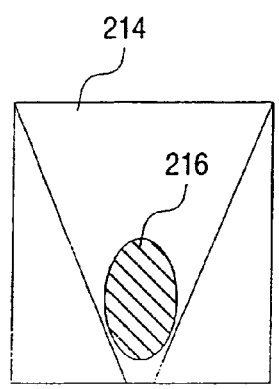
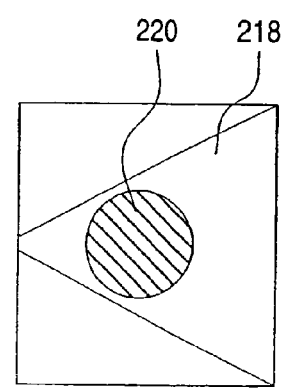
FIG.2A        FIG.2B        FIG.2C
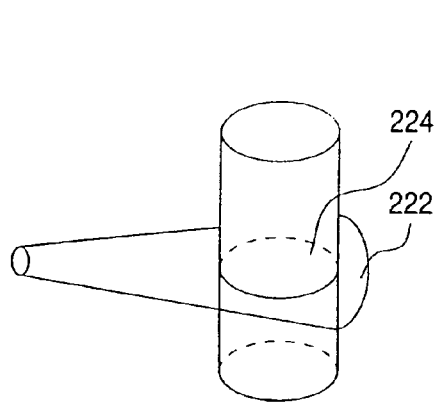
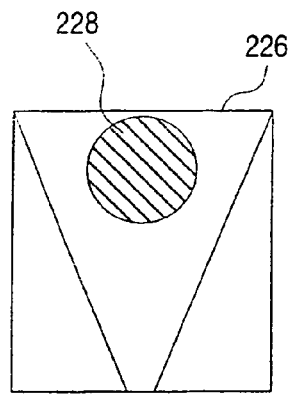
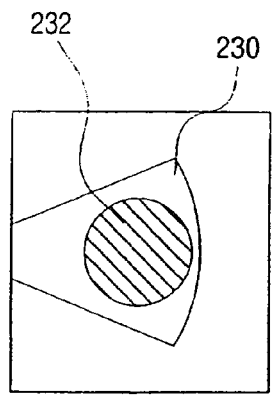
FIG.2D        FIG.2E        FIG.2F

METHOD AND SYSTEM FOR DISPLAYING CROSS-SECTIONAL IMAGES OF A BODY

This application claims the benefit of provisional application No. 60/148,693 filed Aug. 16, 1999.

FIELD AND BACKGROUND OF THE INVENTION

The present invention relates to medical procedures performed with the aid of imaging devices. Some aspects of the present invention relate to medical procedures in which two or more images of different imaging modalities and which are taken simultaneously and/or at different times are used. Other aspects of the present invention relate to the general field known as "Image Guided Surgery". In particular, the present invention relates to a method and system for displaying cross-sectional images of a body so as to render the cross-sectional images more interpretable by a user.

Image guided surgery is well known in the art. In a system described in U.S. Pat. No. 5,772,594 a trajectory of a needle is shown on a fluoroscope image in purpose to navigate the needle to a target. U.S. Pat. No. 5,383,454 describes a system for indicating the position of a surgical probe within a head on a selected cross-sectional image that is the closest to the probe location. U.S. Pat. No. 5,873,822 teaches a system for registering the position of a surgical tool on a prerecorded image. U.S. Pat. No. 5,902,239 shows an improved registration method of a surgical instrument on CT or MRI image.

Fusion of two different images in context of image guided surgery is also well known in prior art. Superimposition of diagnostic and additional lesser-quality CT images is achieved in, for example, U.S. Pat. No. 4,791,934 by adjusting the spatial position and angular orientation of a synthesized image made from one of the original images until an optimum match to the other image is achieved. Positioning an ultrasound image relative to a tomography image using fiducials to form a combined resulting image is described in U.S. Pat. No. 5,810,007. Similarly, WO 96/25882 allows visualization of a final rendering that combines in a co-registered manner two images taken by different imaging modalities. U.S. Pat. Nos. 5,871,445 and 5,891,034 show means to scan a first image and generate a second scanned image which has the same position relative to reference points so that the generated second scanned image corresponds to the particular first scanned image.

Thus, it is well known to generate and use images derived from two imaging modalities and modify such images as if viewed from the same direction at the same scale. In other words, it is known how to generate and use spatially overlapping or fused images even if taken from different angles by different imaging modalities. However, the prior art fails to teach the generation and use of non-overlapping images having a known angular relation there amongst.

There are an increasing number of medical procedures that are performed by inserting a probe into the body, leading the probe to a desired treatment location within the body and spatially applying the treatment at such location via the probe. Typically, in such medical procedures, the maneuvering of the probe within the body is assisted by imaging. Most often, a fluoroscope or an ultrasound imaging device are used, because such imaging devices enable real-time imaging, so as to assist in maneuvering the probe to an appropriate location within the body.

A fluoroscopic image provides comprehensive details of the hard tissues of the body such as bones. It also provides a two-dimensional projection of a volume under imaging, so that each image point is an integral of tissue densities along a line of projection. Although the fluoroscopic image lacks depth perception, it is the preferred imaging tool for navigating a probe to a destination within the body. That is because good imaging quality is achieved for the probe itself, as well as for the skeletal elements of the body which are used as landmarks for navigating the probe. It also gives the practitioner a fair perspective view of the on-going procedure.

Ultrasound imaging, on the other hand, gives a cross-sectional image through the body. Soft tissues are distinguishable, but the picture is much less intuitive and the practitioner is required to have special interpretation skills. The main advantage, but also disadvantage, of the ultrasound is the flexibility in directing the imaging plane. However, such flexibility makes the image rather difficult to comprehend. In order to understand the content of an ultrasound image, the practitioner first has to identify the location and direction of the image slice in the body, which is achieved by identifying some anatomical landmarks. Usually these are cross-sectionals through familiar internal organs. Most of misinterpretation of ultrasound images results from misunderstanding the orientation of the image plane. Hence, planar ultrasounds are less frequently used in procedures in which intra-body navigation of operative tools is performed.

Three dimensional (3D) models made by mathematical manipulation of a plurality of image planes are also taught by the prior art. The time required for gathering the data and computing the model cause such models to be considered as a form of imaging that is not real-time. Lately, attempts to develop a real-time 3D-ultrasound apparatus show initial success. The output display of such a device is a plurality of parallel images along a chosen axis. Yet, by using ultrasound, direct imaging of a tool inside the body is not straightforward due to artifacts presented in the image by such tools. It should be emphasized that in contrary to fluoroscopy, each element of an ultrasound image, regardless of whether such image is planar or 3D, represents a small volume in space, hence may address to a set of coordinates in some reference of coordinates related to the body.

CT (Computerized Tomography) and MRI (Magnetic Resonance Imaging) are often being used for diagnostic purposes, and less in the course of therapeutic procedures, although some versions known as the "Open MRI" or "Interventional MRI" or TMRI (therapeutic MRI) are designed to be used intra-operatively. CT and MRI are typically very expensive and cumbersome to operate, which further limits their use.

The original output data of CT and MRI is a set of paralleled cross-sectional images. Each image element represents a small volume characteristic of the particular modality, known as a "voxel". Mathematically it is possible to manipulate the data to produce an image plane that is of a different direction or spatial location from the original cross-sectionals. Another possibility is, using special filtering, to render a 3D model of a particular characteristic of the data such as the vascular system, bones, tumor, cavities, etc.

Since each of the different-imaging modalities identifies different types and characters of tissues, it is of great advantage to use a plurality of imaging modalities simultaneously. In doing so, it is very important to maintain the practitioner's depth perception and interpretation skills at the highest possible level. There is thus a widely recognized need for, and it would be highly advantageous to have a method and system for displaying cross-sectional images of a body so as to render the cross-sectional images more interpretable by a user.

SUMMARY OF THE INVENTION

According to one aspect of the present invention there is provided a method of displaying cross-sectional images of a body so as to render the cross-sectional images more interpretable, the method comprising the steps of (a) using a first imaging device, obtaining at least one cross-sectional image of a portion of the body, the at least one cross-sectional image being defined by at least one first plane; and (b) projecting each of the at least one cross-sectional image of the portion of the body onto a predefined second plane, so as to obtain at least one projected cross-sectional image of the portion of the body, each of the at least one projected cross-sectional image becoming more interpretable by a user.

According to another aspect of the present invention there is provided a system for displaying cross-sectional images of a body so as to render the cross sectional images more interpretable, the system comprising (a) a first imaging device for obtaining at least one cross-sectional image of a portion of the body, the at least one cross-sectional image being defined by at least one first plane; and (b) a projection and display mechanism for projecting each of the at least one cross-sectional image of the portion of the body onto a predefined second plane, so as to obtain and display at least one projected cross-sectional image of the portion of the body, each of the at least one projected cross-sectional image becoming more interpretable by a user.

According to yet another aspect of the present invention there is provided a method of displaying a three dimensional image rendered from a is plurality of consecutive cross-sectional images of a body so as to render the rendered image more interpretable, the method comprising the steps of (a) using a first imaging device, obtaining a plurality of consecutive cross-sectional images of a portion of the body, each of the plurality of consecutive cross-sectional images being defined by a plane; (b) rendering the plurality of consecutive cross-sectional images of the portion of the body into a rendered three dimensional model image of the portion of the body; and (b) projecting the rendered three dimensional model image as if viewed following a line-of-sight of a second imaging device used to image the body.

According to still another aspect of the present invention there is provided a system for displaying a three dimensional image rendered from a plurality of consecutive cross-sectional images of a body so as to render the rendered image more interpretable, the system comprising (a) a first imaging device for obtaining a plurality of consecutive cross-sectional images of a portion of the body, each of the plurality of consecutive cross-sectional images being defined by a plane; (b) a rendering device for rendering the plurality of consecutive cross-sectional images of the portion of the body into a rendered three dimensional model image of the portion of the body; and (b) a projecting and displaying device for projecting and displaying the rendered three dimensional model image as if viewed following a line-of-sight of a second imaging device used to image the body.

According to further features in preferred embodiments of the invention described below, the first imaging device is a single plane imaging device.

According to still further features in the described preferred embodiments the single plane imaging device is a single plane ultrasound device.

According to still further features in the described preferred embodiments the single plane ultrasound device is an intrabody single plane ultrasound device.

According to still further features in the described preferred embodiments the single plane ultrasound device is an extra-body single plane ultrasound device.

According to still further features in the described preferred embodiments the first imaging device is a multiple plane imaging device.

According to still further features in the described preferred embodiments the multiple plane imaging device is selected from the group consisting of a positron emission tomography device, a computerized tomography device, a magnetic resonance imaging device and a three dimensional-ultrasound device.

According to still further features in the described preferred embodiments the predefined second plane is at a pre selected angle to a line-of-sight of a second imaging device used to image the body.

According to still further features in the described preferred embodiments the second imaging device is selected from the group consisting of a fluoroscope, a positron emission tomography device, a computerized tomography device, a magnetic resonance imaging device and a three dimensional-ultrasound device.

According to still further features in the described preferred embodiments the predefined second plane coincides with the line-of-sight.

According to still further features in the described preferred embodiments the predefined second plane is perpendicular to the line-of-sight.

According to still further features in the described preferred embodiments projecting each of the at least one cross-sectional image of the portion of the body by the projection and display mechanism onto the predefined second plane is effected by (i) establishing a location and orientation of each of the first plane in six degrees of freedom; (ii) establishing a location and orientation of the predefined second plane in six degrees of freedom; and (iii) projecting each of the first plane onto the second predefined plane, thereby projecting each of the cross-sectional image of the portion of the body onto the predefined second plane.

According to still further features in the described preferred embodiments the system further comprising a locating system, wherein establishing the location and orientation of each of the first plane in six degrees of freedom is effected by a first locating sensor of the locating system, the first locating sensor is implemented on the first imaging device.

According to still further features in the described preferred embodiments the predefined second plane is at a pre selected angle to a line-of-sight of a second imaging device used to image the body.

According to still further features in the described preferred embodiments establishing the location and orientation of the predefined second plane in six degrees of freedom is effected by a second locating sensor of the locating system, the second locating sensor is implemented on the second imaging device.

The present invention successfully addresses the shortcomings of the presently known configurations by providing for projection of cross-sectional images of the body onto a common plane, so as to render such images more interpretable by a user.

Implementation of the method and system for displaying cross-sectional images of a body so as to render the cross-sectional images more interpretable of the present invention involves performing or completing selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 2*a–f* is a schematic depiction demonstrating image projection in accordance with the teachings of the present invention.

DESCRIPTION OF THE PREFERRED EMBODIMENTS

Figure 1:
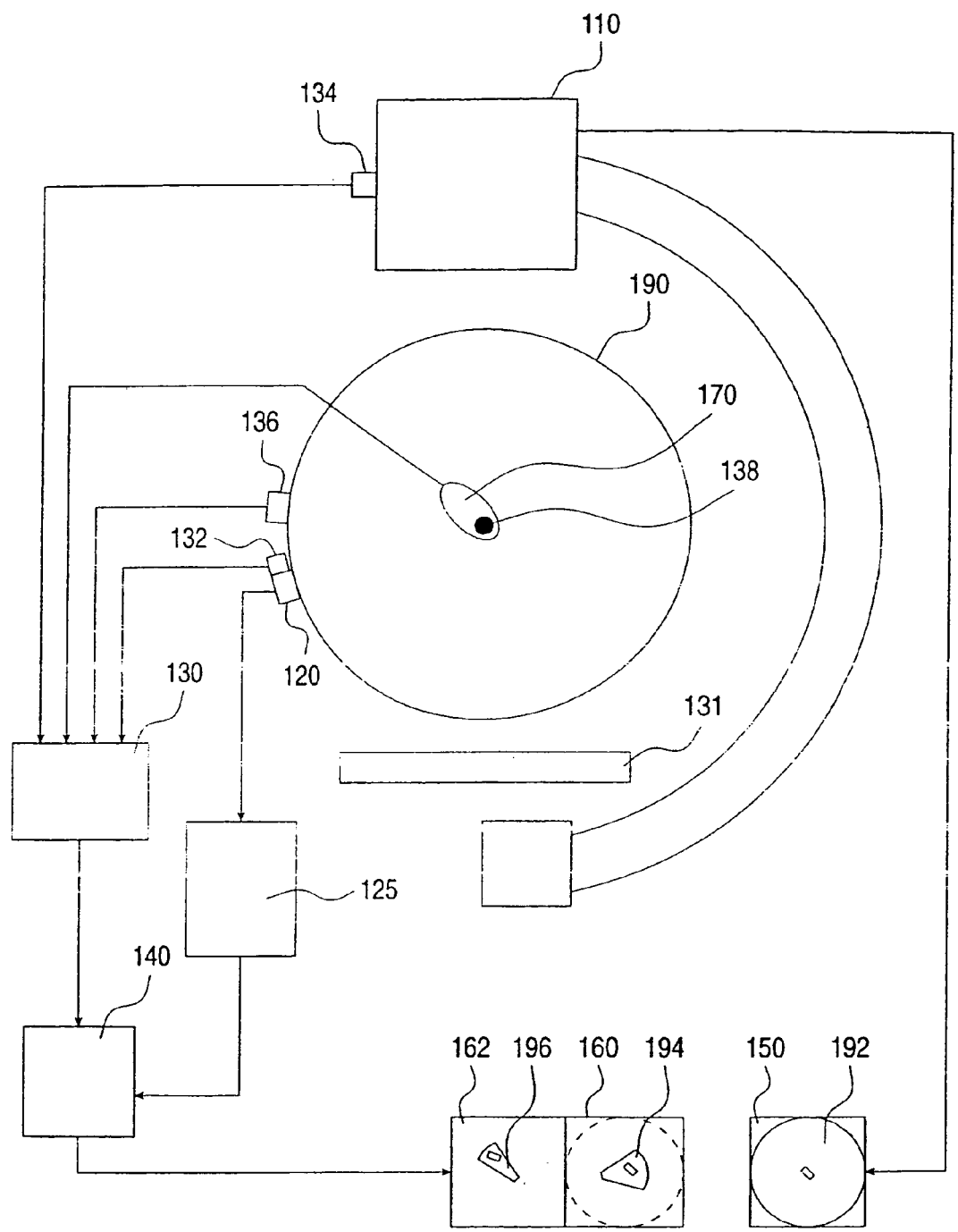
FIG. 1 is a schematic depiction of a system according to one aspect of the present invention.

The invention is of a method and system for displaying cross-sectional images of a body, which can be used to render the cross-sectional images more interpretable by a user. Specifically, the present invention can be used to project a plurality of cross-sectional images onto a common predefined plane, which, for example, coincides, or is perpendicular to, a line-of-sight of, for example, a trans-luminance imaging device, such as a fluoroscope.

The principles and operation of a method and system according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Thus, according to one aspect of the present invention there is provided a method of displaying cross-sectional images of a body so as to render the cross-sectional images more interpretable. The method according to this aspect of the present invention is effected by implementing the following method steps, in which, in a first step, a first imaging device is used for obtaining at least one cross-sectional image of a portion of the body which is defined by a first plane. In a second step of the method according to the present invention, each of the at least one cross-sectional images of the portion of the body is projected onto a predefined second plane, so as to obtain at least one projected cross-sectional image of the portion of the body. Each of the at least one projected cross-sectional images thus becomes more interpretable by a user.

According to another aspect of the present invention there is provided a system for displaying cross-sectional images of a body so as to render the cross-sectional images more interpretable. The system according to this aspect of the present invention includes a first imaging device for obtaining at least one cross-sectional image of a portion of the body which is defined by at least one first plane. The system according to this aspect of the present invention further includes a projection and display mechanism for projecting each of the at least one cross-sectional image of the portion of the body onto a predefined second plane, so as to obtain and display at least one projected cross-sectional image of the portion of the body. Each of the at least one projected cross-sectional images thus becomes more interpretable by a user.

The first imaging device which can be used to implement the present invention can be, for example, a single plane imaging device, such as a single plane intra-body or extra-body ultrasound device, or a multiple plane imaging device such as a three dimensional-ultrasound device (either real-time or non real-time), positron emission tomography (PET) device, a computerized tomography (CT) device or a magnetic resonance imaging (MRI) device, such as an open, interventional or therapeutic MRI device.

According to a preferred embodiment of the present invention the predefined second plane is at a pre selected angle to a line-of-sight of a second imaging device used to image the body. Thus, for example, the predefined second plane can coincide with the line-of-sight of the second imaging device.

Alternatively, or in addition, the predefined second plane can be perpendicular to the line-of-sight of the second imaging device. The second imaging device can be, for example, a multiple plane imaging device, which provides a plurality of consecutive cross-sectional images of the body, examples thereof are listed above with respect to the first imaging device, or it can alternatively and presently preferably be a trans-luminance imaging device such as a fluoroscope.

Projecting each of the at least one cross-sectional images of the portion of the body by the projection and display mechanism onto the predefined second plane is effected by establishing a location and orientation of each of the first planes in six degrees of freedom: establishing a location and orientation of the predefined second plane in six degrees of freedom; and projecting each of the first plane onto the second predefined plane, thereby projecting each of the cross-sectional image of the portion of the body onto the predefined second plane. As is further detailed below, establishing these locations can be effected by, for example, a locating system having locating sensors or implements implemented on the first and second imaging devices.

According to yet another aspect of the present invention there is provided a method of displaying a three-dimensional image rendered from a plurality of consecutive cross-sectional images of a body so as to render the rendered image more interpretable by a user. The method according to this aspect of the present invention is effected by implementing the following method steps, in which, in a first step, a first imaging device is used for obtaining a plurality of consecutive cross-sectional images of a portion of the body. Each of the plurality of consecutive cross-sectional images being is defined by a plane. In a second step of the method according to this aspect of the present invention the plurality of consecutive cross-sectional images of the portion of the body are rendered into a three dimensional model image of the portion of the body. Finally, the rendered three-dimensional model image is projected as if viewed following a line-of-sight of a second imaging device used to image the body.

According to still another aspect of the present invention there is provided a system for displaying a three dimensional image rendered from a plurality of consecutive cross-sectional images of a body so as to render the rendered image more interpretable by a user. The system according to this aspect of the present invention includes a first imaging device for obtaining a plurality of consecutive cross-sectional images of a portion of the body. Each of the plurality of consecutive cross-sectional images being defined by a plane. The system further includes a rendering device, such as a computer, for rendering the plurality of consecutive cross-sectional images of the portion of the body into a rendered three-dimensional model image of the portion of the body. The system according to this aspect of the present invention further includes a projecting and displaying device for projecting and displaying the rendered three dimensional model image as if viewed following a line-of-sight of a second imaging device used to image the body. Rendering software is well known in the art and requires no further description herein.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non-limiting fashion.

In some medical procedures a probe has to be manipulated within the body under imaging. As used herein the term "probe" refers in general to any medical tool, for external and/or internal use, such as catheters and guide-wires for use in blood vessels, surgical tools such as scalpels, pincers, orthopedic pins and screws, etc. Traditionally, the navigation of such a probe within the body is performed under real-time imaging by a primary imaging (referred to hereinabove and in the claims as the second imaging device) in order to orient the probe relative to the internal tissues of body. In some cases, a secondary imaging device (referred to hereinabove and in the claims as the first imaging device), which is preferably complementing in its characteristics to the primary imaging device, is also employed in context of the primary imaging device's display. The primary imaging is used for orientation and navigation and the secondary imaging is used for enhancing the information that is lacking in the primary imaging. Typically, the primary imaging device displays a volume image or a trans-luminance image of the body. Preferably, the primary imaging device is a fluoroscope, since it provides a real-time perspective view through the body, including hard tissues as well as the probe in use. However, as is further detailed above, CT, PET, MRI or 3D-ultrasound may also be used, either as a plurality of sequential image planes or as a 3D rendered model of an internal organ. In any case, the primary imaging device defines a preferred line of sight (PLOS). This line of sight is constant throughout prolonged time periods or the entire medical procedure and is therefore suitable as a reference for interpretation of images of the secondary imaging device. However, in order for the preferred line of sight to serve as such a reference, the secondary image(s) must first be projected onto a plane having a known, predefined, relation thereto.

In some embodiments the PLOS has a fixed orientation relative to the body of the patient, in this case, the secondary image is projected onto a plane which represents a fixed slice of the body.

For having the necessary data needed to project the secondary image, it is required to measure the six degrees of freedom (6 DOF) orientation of both imaging devices. In order to navigate a probe intra-bodily, it is also required to track the 6 DOF orientation of the probe or of the patient's body. Some methods and apparatuses well described in the prior art references listed in the Background section may be suitable for this task. Other systems for tracking the position and angular orientation of an object in 6 DOF are also well known in the art. For example, U.S. Pat. No. 5,558,091, WO 96/05768 and PCT/IL99/00371 teach a locating sensor which comprises of a plurality of miniature coils, to sense at least three electromagnetic fields induced by plurality of antennae that are placed externally to the body. These systems measure the location and direction of the locating sensor at 6 DOF relative to a reference frame of coordinates defined by the antennae. By implementing a sensor into a treatment-applying probe, it is possible to measure its 6 DOF orientation relative to the reference frame of coordinates. By attaching another locating sensor to the body of the patient, movement of the body during the procedure may be compensated. Furthermore, by attaching a third sensor to an imaging device, measurement of the imager line of sight may be performed.

Example 1

FIG. 1 shows a system having a fluoroscope 110 which is used as a primary imager. Its output image 192 is displayed on a monitor 192. A single plane ultrasound transducer 120 is used as a secondary imager. Transducer 120 may be of an external type, imaging from the skin of the patient, or of an internal type (such as TEE or IVUS or ICUS), imaging from the interior of the patient's body. In any case, transducer 120 is moving in free hand. A first locating sensor 134 is attached to the frame of the fluoroscope. A second locating sensor 132 is attached to, or embedded into, transducer 120. A third locating sensor 138 is embedded into a treatment-applying probe 170. A fourth locating sensor 136 is attached to the body of the patient (it may also be located within the body). A locating system 130 feeds three low frequency current signals to antennae 131. All four locating sensors 132, 134, 136, 138 are sensing the induced electromagnetic fields, and the sensed signals are fed to system 130. Locating system 130 calculates the 6 DOF orientation of the locating sensors, and its results are fed to a computer 140 (preferably a PC type). Ultrasound imaging system 125 is operating transducer 120, receiving its signals and generating an output image of a cross-sectional scan 190 of the body. Its output is fed to a frame grabber that forms a part of computer 130. The ultrasound image may be displayed directly or after mathematical manipulations on a display 160.

Antennae 131 define a reference frame of coordinates. Since locating sensor 134 is attached to the frame of fluoroscope 116, measuring in 6 DOF the location and orientation of sensor 134 is, in effect, equivalent to measuring the location and orientation of the fluoroscope image relative to the reference frame of coordinates. Similarly, measuring in 6 DOF the location and orientation of sensor 132, which is attached to transducer 120, is, in effect, equivalent to measuring the location and orientation of ultrasound scan 190 in the reference frame of coordinates. Also, since locating sensor 138 is embedded in probe 190, measuring in 6 DOF the location and orientation of sensor 138 is, in effect, equivalent to measuring the location and orientation of probe 170.

Calibration of the system should be performed prior to use. First, fluoroscope 110 is directed vertically, and moved so that the image of probe 138 is centered. Arbitrarily, at this setup, the 6 DOF orientation of sensor 134 is defined as the origin of the reference frame of coordinates system. Then, ultrasound system 125 is operated to image the tip of probe 138. The coordinates of probe 138 in image 190 are measured, for instance, by displaying image 190 on computer display 160 and using a computer mouse (not shown). Simultaneously, the locations and orientations of sensors 132 and 138 are also measured. The same sequence is repeated two more times, to have a total of three points in which the coordinates of the points are measured by locating system 130, as well, as by ultrasound system 125. Since three points define a plane in space, this is sufficient information for calibrating the initial direction of image 190, which is defined in the reference frame of coordinates.

There are other, even simpler methods to calibrate the system. For example, phantoms can be used to calibrate the ultrasound and fluoroscope imaging systems. Another calibration can be executed by positioning the fluoroscope at a vertical (anterior-posterior) direction and bringing the tip of the imaging probe to the center of the fluoroscope image and measuring the position and orientation of the sensors.

Operating the system during a medical procedure, a program in the computer is calculating the projection of the ultrasound cross-sectional image to the orientation of the PLOS. A simple example, in reference to FIGS. 2*a* –*f*, may demonstrate the method. Let a tube 200 lay along the direction of PLOS 205, as shown in FIG. 2*a*. Suppose that a transducer 202 is handled to be close to the tube, and tilted to have an image plane 210 in an angle relative to tube 200. FIG. 2*b* shows the resulting non-projected image, in which cross-sectional 216 of tube 205 appears as an oval shape at the bottom of the image. In FIG. 2*c*, the projection of the image to the orientation of the PLOS appears as a circle 220 centered in the middle of the display. Changing the orientation of transducer 202 to be farther away and in a right angle relative to to tube 200, as can be seen in FIG. 2*d*, results in an image in the shape of a circle 228 at the top of the non-projecting image as shown in FIG. 2*e* Projecting the image to the orientation of PLOS results in a circle 232 at the center of the image shown in FIG. 2*f*.

As can be easily understood from this simple example, by changing the orientation of the ultrasound transducer the shape and location of image elements are significantly changing. Once projection to any external reference of coordinates is applied, the location and shape of object is maintained as if viewed from externally to the body, hence greatly increasing the comprehensiveness and stability of the image. Depending on the mutual direction between PLOS and orientation of the transducer, part, and sometimes all, of the information in the ultrasound image may be lost in projection. Hence it is preferable to add another viewing angle that is perpendicular to PLOS orientation to which another projection be performed, be displayed on display 162, side by side to display 160, such that during a medical procedure, ultrasound image 190 is projected onto two perpendicular image planes, preferably, but not necessarily, one of the two is in the orientation of PLOS.

The projection of probe 170 may be displayed as a graphic symbol image on displays 160 and 162, by projecting the coordinates of sensor 138 from the reference system of coordinates to PLOS system of coordinates. In the course of navigating the probe in the body, it is often beneficial to mark locations in which the probe is located (being of some special interest for enhancing the efficiency of the procedure). Points of interest are taken simply by memorizing the 6 DOF location and orientation of the probe and a reference sensor 136 that is attached to body of the patient. Such points of interest may be presented on display 160 and, if applicable, also on display 162. Landmarks of special interest may also be taken, marked from the ultrasound image, as each point in the ultrasound image corresponds to a location in a 3D space relative to the reference frame of coordinates. Such landmarks also have to be coupled with the location and orientation of reference sensor 136. In the course of the procedure, if the location or angular orientation of the body of the patient, or the primary imaging device, or the secondary imaging device, were changed, the display of such point and landmark of interest is automatically corrected to match the actual original intra-body location, as if displayed from current imaging orientation. Therefore if the probe will be navigated back to such a point of interest such that its computer-graphic image coincides with a marking of a point of interest, it will be placed accurately at the location in the body where the point of interest had originally been recorded. Further details relating to acquiring points of interest can be found in PCT/IL99/00512, which is incorporated herein by reference.

Example 2

This Example provides a system similar to that described under Example 1 hereinabove, except that ultrasound system 125 and ultrasound transducer 120 form a real-time 3D ultrasound imaging system. Computer 140 is programmed to produce a 3D rendered model from the ultrasound data. The rendered picture 194 is produced as if seen from the direction of the PLOS, to be displayed on display 160. The rendered picture 196 is may additionally be produced as if seen from a direction perpendicular to the PLOS, to be displayed on display 162.

Example 3

Figure 3:
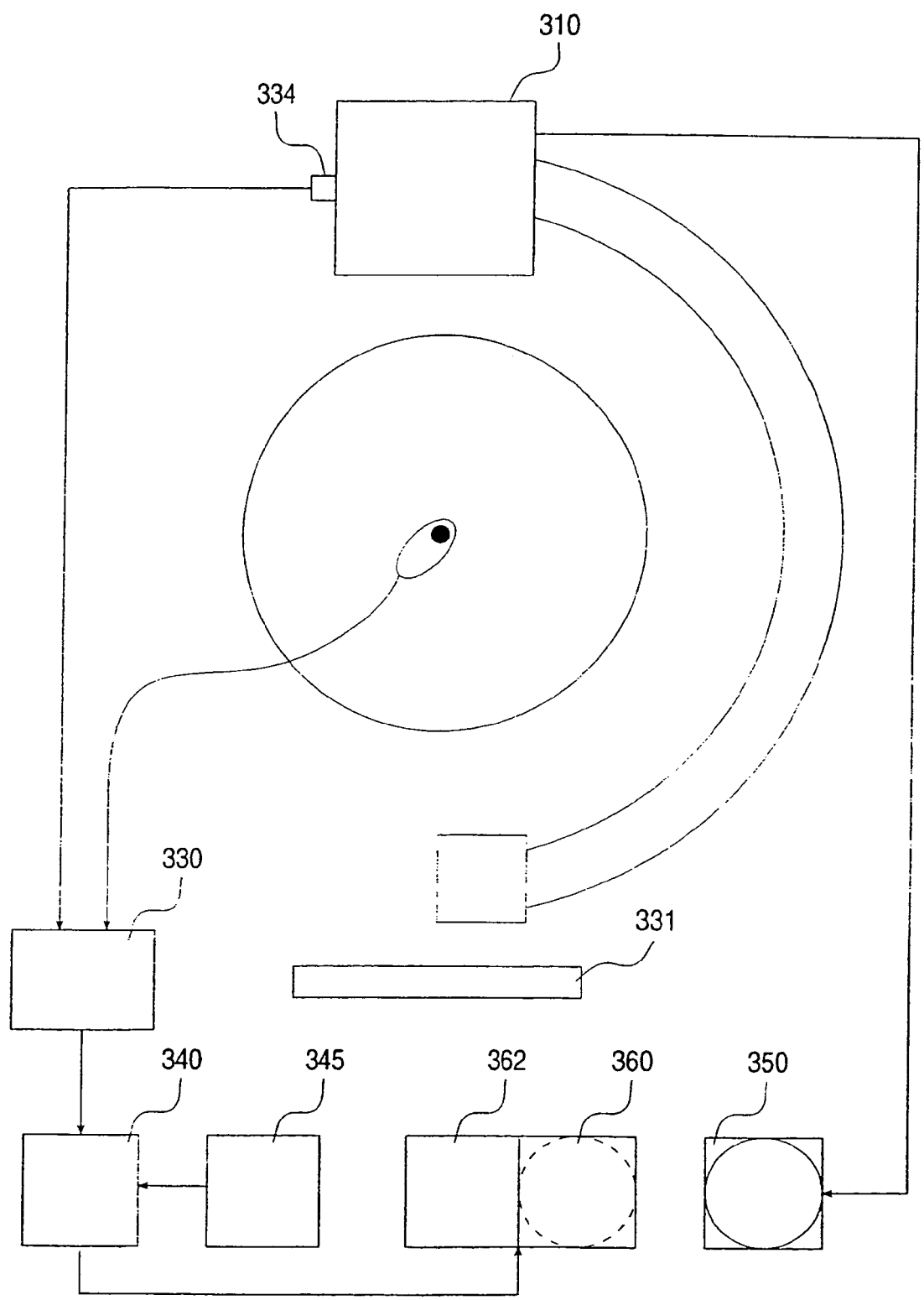
FIG. 3 is a schematic depiction of a system according to another aspect of the present invention.

FIG. 3 shows yet another system in accordance with the teachings of the present invention having a fluoroscope, which is again used as a primary imaging device. A fluoroscopic image 392 is displayed on display 350. CT, MRI or 3D-ultrasound device serves as a secondary imaging device. However, as opposed to the former two examples, the images thereof were previously-taken. Locating system 330 feeds low frequency current signals to antennae 331. Locating sensor 334 senses the electromagnetic signals that are induced by the antennae and feeds these signals to locating system 330. Locating system 330 calculates in 6 DOF the location and orientation of the fluoroscope relative to a reference system of coordinates that is defined by, for example, antennae 331. A locating sensor 338 implemented into a probe 370 also senses the electromagnetic fields, feeds them to system 330, so that the location and orientation in 6 DOF of probe 370 is also calculated. The resulting locations and orientations are fed by system 330 to a computer 340. Memory module 345, containing an MRI, CT or 3D ultrasound image of the patient is connected to the computer, hence dedicated software running on the computer calculates a cross-sectional image plane of a desired spatial location and angular orientation of the patient. Having PLOS defined by the location and orientation of sensor 334, projection of the cross-sectional image in the direction of PLOS is computed, to be displayed on display 360. Initial calibration of PLOS is performed as in Example 1. Registration of the secondary image data to the reference system of coordinates is performed by pointing probe 370 on at least three points that may be recognized either by naked eye or by using the fluoroscope to obtain at least three pairs of coordinates. Each pair of coordinates includes one member measured at the reference system of coordinates, and another member measured at the secondary imaging data.

Prior to performing the medical procedure, a cross-sectional image is chosen to be displayed on display 360. In the course of the procedure this cross-sectional image is projected on a plane having a known relation, e.g., coincide with, and/or perpendicular to, the PLOS. These images are displayable on displays 360 and 362. Landmarks and points of interest that are marked in the same method as explained under Example 1 may also be displayed on displays 360, 362 and/or 350.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications cited herein are incorporated by reference in their entirety.

What is claimed is:

1. A method of displaying cross-sectional images of a body so as to render the cross-sectional images more interpretable, the method comprising the steps of:
    (a) using a first intra-body imaging device deployed on a flexible catheter, obtaining at least one cross sectional image of a portion of the body, said at least one cross sectional image being defined by at least one first plane;
    (b) employing an inductive electromagnetic-field-sensing position-measuring system, including a locating sensor implemented on said first imaging device, to establish a location and orientation of each of said first plane in six degrees of freedom; and
    (c) projecting each of said at least one cross-sectional image of said portion of the body onto a predefined second plane, so as to obtain at least one projected cross-sectional image of said portion of the body, each of said at least one projected cross-sectional image becoming more interpretable by a user.

2. The method of claim 1, wherein said first imaging device is a single plane imaging device.

3. The method of claim 2, wherein said single plane imaging device is a single plane ultrasound device.

4. The method of claim 3, wherein said single plane ultrasound device is an intrabody single plane ultrasound device.

5. The method of claim 1, wherein said first imaging device is a multiple plane imaging device.

6. The method of claim 1, wherein said predefined second plane is at a preselected angle to a line-of-sight of a second imaging device used to image the body.

7. The method of claim 6, wherein said second imaging device is selected from the group consisting of a fluoroscope, a positron emission tomography device, a computerized tomography device, a magnetic resonance imaging device and a three dimensional-ultrasound device.

8. The method of claim 6, wherein said predefined second plane coincides with said line-of-sight.

9. The method of claim 6, wherein said predefined second plane is perpendicular to said line-of-sight.

10. The method of claim 1, wherein projecting each of said at least one cross-sectional image of said portion of the body onto said predefined second plane is effected by:
    (i) establishing a location and orientation of said predefined second plane in six degrees of freedom; and
    (ii) projecting each of said first plane onto said second predefined plane, thereby projecting each of said cross sectional image of said portion of the body onto said predefined second plane.

11. The method of claim 10, wherein said predefined second plane is at a pre selected angle to a line-of-sight of a second imaging device used to image the body.

12. The method of claim 11, wherein establishing said location and orientation of said predefined second plane in six degrees of freedom is effected by a locating sensor implemented on said second imaging device.

13. A method of displaying a three dimensional image rendered from a plurality of consecutive cross-sectional images of a body so as to render the rendered image more interpretable, the method comprising the steps of:
    (a) using a first intra-body imaging device deployed on a flexible catheter, obtaining a plurality of consecutive cross-sectional images of a portion of the body, each of said plurality of consecutive cross-sectional images being defined by a plane;
    (b) employing a position-measuring system, including a locating sensor implemented on said first imaging device, to establish a location and orientation of each of said planes in six degrees of freedom;
    (c) rendering said plurality of consecutive cross-sectional images of said portion of the body into a rendered three dimensional model image of said portion of the body; and
    (d) projecting said rendered three dimensional model image as if viewed following a line-of-sight of a second imaging device used to image the body.

14. The method of claim 13, wherein said position-measuring system is an inductive electromagnetic-field-sensing position-measuring system.

15. A system for displaying a three dimensional image rendered from a plurality of consecutive cross-sectional images of a body so as to render the rendered image more interpretable, the system comprising:
    (a) a first intra-body imaging device deployed on a flexible catheter for obtaining a plurality of consecutive cross-sectional images of a portion of the body, each of said plurality of consecutive cross-sectional images being defined by a plane;
    (b) a position-measuring system including a locating sensor implemented on said first imaging device, said position-measuring system determining a location and orientation of each of said planes in six degrees of freedom;

(c) a rendering device for rendering said plurality of consecutive cross-sectional images of said portion of the body into a rendered three dimensional model image of said portion of the body; and (d) a projecting and displaying device for projecting and displaying said rendered three dimensional model image as if viewed following a line-of-sight of a second imaging device used to image the body.

16. The system of claim 15, wherein said position-measuring system is an inductive electromagnetic-field-sensing position-measuring system.

* * * * *